United States Patent
Brigstock et al.

(10) Patent No.: US 11,180,810 B2
(45) Date of Patent: Nov. 23, 2021

(54) METHODS FOR DETECTING HEPATIC FIBROSIS AND RESPONSIVENESS TO THERAPY

(71) Applicants: RESEARCH INSTITUTE AT NATIONWIDE CHILDREN'S HOSPITAL, Columbus, OH (US); BEIJING FRIENDSHIP HOSPITAL, CAPITAL MEDICAL UNIVERSITY, Beijing (CN)

(72) Inventors: David Brigstock, Dublin, OH (US); Li Chen, Dublin, OH (US); Hong You, Beijing (CN); Min Cong, Beijing (CN)

(73) Assignees: RESEARCH INSTITUTE AT NATIONWIDE CHILDREN'S HOSPITAL, Columbus, OH (US); BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 202 days.

(21) Appl. No.: 15/764,284

(22) PCT Filed: Sep. 28, 2016

(86) PCT No.: PCT/US2016/054215
§ 371 (c)(1),
(2) Date: Mar. 28, 2018

(87) PCT Pub. No.: WO2017/058938
PCT Pub. Date: Apr. 6, 2017

(65) Prior Publication Data
US 2018/0282810 A1    Oct. 4, 2018

Related U.S. Application Data

(60) Provisional application No. 62/234,581, filed on Sep. 29, 2015.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2009/0176723 A1 | 7/2009 | Brown et al. |
| 2010/0151480 A1 | 6/2010 | Taylor et al. |
| 2013/0078225 A1 | 3/2013 | Zeng et al. |
| 2013/0150426 A1 | 6/2013 | Kossen et al. |
| 2014/0121133 A1* | 5/2014 | Zhang ................. C12Q 1/6809 506/16 |
| 2015/0024961 A1 | 1/2015 | Klass et al. |
| 2015/0031574 A1* | 1/2015 | Murakami ............ C12Q 1/706 506/9 |
| 2015/0301058 A1 | 10/2015 | Schettini et al. |
| 2016/0108368 A1 | 4/2016 | Larocca et al. |
| 2017/0298352 A1 | 10/2017 | Brigstock et al. |

FOREIGN PATENT DOCUMENTS

| | | |
|---|---|---|
| WO | WO-2011/143499 A1 | 11/2011 |
| WO | WO-2014/036429 A1 | 3/2014 |
| WO | WO-2014/100252 A1 | 6/2014 |
| WO | WO-2015/112382 A1 | 7/2015 |

OTHER PUBLICATIONS

Tumilson et al. Molecular Neurobiology. 2014. 50: 545-558 (Year: 2014).*
Tian et al. PLoS One. Jan. 5, 2012. 7(1): e29551 (Year: 2012).*
Zhou et al Scientific Reports. Jun. 10, 2015. 6:11251 (Year: 2015).*
Gene Expression Omnibus (GEO) GSE33857. Available via URL: < ncbi.nlm.nih.gov/geo/query/acc.cgi?acc=GSE33857>, 2 pages, printed on Jul. 13, 2020 (Year: 2020).*
Gene Expression Omnibus (GEO) Platform GPL106546. Aavailable via URL: < ncbi.nlm.nih.gov/geo/query/acc.cgi?view=data&acc=GPL10656&id=24712&db=GeoDb_blob63, 18 pages, printed on Jul. 13, 2020 (Year: 2020).*
Stratech. "Exosome Antibodies, Arrays and ELISA Kits Detecta and quantitate isolated exosomes", Feb. 7, 2014., p. 1-11, available via URL: <www.stratech.co.uk/sbi/exosomes/> (Year: 2014).*
Chen, L. et al. (2013) "Exosomal microRNA modulates pathways of liver fibrosis by regulating connective tissue growth factor (CTGF) expression in fibrogenic cells during chronic injury," The FASEB Journal 27(1):1b440.
Chen, L. et al. (2014) "Determination of signature microRNAs in experimental liver fibrosis by miRnome profiling of circulating exosomes," Molecular Biology of the Cell 25:P1578.
Chen, L. et al. (2014) "MicroRNA profiling of circulating exosomes during experimental liver fibrosis," Hepatology 60(1) Sp. Iss. Sl, 430:412A.
Cong, M. et al. (2015) "MicroRNA profiling of circulating exosomes in HBV cirrhosis patients following anti-HBV therapy," Hepatology 62(1):896A.
Murakami, Y. et al. (2012) "Comprehensive miRNA Expression Analysis in Peripheral Blood Can Diagnose Liver Disease," PLoS ONE 7(10):e48366.
Sole, C. et al. (2015) miR-29c in urinary exosomes as predictor of early renal fibrosis in lupus nephritis, Nephrol Dial Transplant 30:1488-1496.

(Continued)

*Primary Examiner* — Carla J Myers
(74) *Attorney, Agent, or Firm* — Foley & Lardner LLP (57) ABSTRACT

This disclosure provides kits and methods for determining whether a subject is suffering from a liver disease, and/or whether the subject will be a responsive to a therapy for a liver disease. The disclosed methods comprise determining the miR profile of exosomes isolated from a body fluid of the subject.

21 Claims, 2 Drawing Sheets

(56) References Cited

OTHER PUBLICATIONS

Wang, H. et al. (2014) "Expression of Serum Exosomal MicroRNA-21 in Human Hepatocellular Carcinoma," BioMed Research International 1820(4):940-945.
International Search Report and Written Opinion (ISA/EP) for International Application No. PCT/US2016/054215, dated Jan. 31, 2017.
U.S. Appl. No. 16/794,066, filed Feb. 18, 2020, Research Institute at Nationwide Children's Hospital.
Akamatsu et al., "Differences in serum microRNA profiles in hepatitis B and C virus infection", Journal of Infection (2015) 70, pp. 273-287.
Bihrer et al., "Serum miR-122 as a Biomarker of Necroinflammation in Patients With Chronic Hepatitis C Virus Infection", The American Journal of Gastroenterology, vol. 106, Sep. 2011, pp. 1663-1669.
Brigstock DR (2014) Riding the exosome shuttle in the liver. Cleveland Clinic, Cleveland OH May 20, 2014. Invited speaker.
Chen L, Chen R, Brigstock DR (2014) Determination of signature microRNAs in experimental liver fibrosis by miRnome profiling of circulating exosomes Mol Biol Cell 25 (suppl) P1578.
Chen L, Chen R, Brigstock DR (2014) MicroRNA profiling of circulating exosomes during experimental liver fibrosis. Hepatology 60 1 (Suppl) Abstract #430 p. 412A.
Cong M, Chen L, Liu T, Wang P, Jia J, Brigstock D, You H (2015) MicroRNA profiling of circulating exosomes in HBV cirrhosis patients following anti-HBV therapy. Hepatology 62 (Suppl) A1404 p896A.
Fang et al., "Circulating microRNAs as biomarkers for diffuse myocardial fibrosis in patients with hypertrophic cardiomyopathy", Journal of Translational Medicine, 2015, 13, pp. 1-12.
Jazbutyte et al., "MicroRNA-22 increases senescence and activates cardiac fibroblasts in the aging heart", AGE, (2013), 35, pp. 747-762.
Ji et al., "Circulating microRNAs in hepatitis B virus-infected patients", Journal of Viral Hepatitis, 2011, 18, e242-e251.
Ji et al., "MiR-22 Suppresses BMP7 in the Development of Cirrhosis", Cellular Physiology and Biochemistry, Jun. 16, 2015, 36, pp. 1026-1036.
Jiang et al., "miR-22 Promotes HBV-Related Hepatocellular Carcinoma Development in Males", American Association for Cancer Research, Jul. 12, 2011, pp. 5593-5603.
Lopez-Riera et al., "New microRNA Biomarkers for Drug-Induced Steatosis and Their Potential to Predict the Contribution of Drugs to Non-alcoholic Fatty Liver Disease", Frontiers in Pharmacology, Jan. 2017, vol. 8, Article 3, pp. 1-12.
Makino et al., "The Downregulation of microRNA let-7a Contributes to the Excessive Expression of Type I Collagen in Systemic and Localized Scleroderma", The Journal of Immunology, 2013, 190, pp. 3905-3915.
Roy et al., "miR-30c and miR-193 are a part of the TGF-Beta-dependent regulatory network controlling extracellular matrix genes in liver fibrosis", Journal of Digestive Diseases, 2015, 16, pp. 513-524.
Shen et al., "microRNA-222 modulates liver fibrosis in a murine model of biliary atresia", Biochemical and Biophysical Research Communications, 446 (2014), pp. 155-159.
Shi et al., "MicroRNA-22 is down-regulated in hepatitis B virus-related hepatocellular carcinoma", Biomedicine & Pharmacotherapy, 67 (2013), pp. 375-380.
Vuppalanchi et al., "Relationship between Differential Hepatic microRNA Expression and Decreased Hepatic Cytochrome P450 3A Activity in Cirrhosis", PLoS One, Sep. 2013, vol. 8, Issue 9, e74471, pp. 1-9.
Yang et al., "ChIPBase: a database for decoding the transcriptional regulation of long non-coding RNA and microRNA genes from ChIP-Seq data", Nucleic Acids Research, vol. 41, Nov. 17, 2012, pp. D177-D187.
Zhang et al., "Identification and study of differentially expressed miRNAs in aged NAFLD rats based on high-throughput sequencing", Annals of Hepatology, 19 (2020), pp. 302-312.
Zlotogorski-Hurvitz et al. Human saliva-derived exosomes: comparing methods of isolation. J Histochem Cytochem. 2015; 63(3):181-189 Epub Dec. 3, 2014.

* cited by examiner

METHODS FOR DETECTING HEPATIC FIBROSIS AND RESPONSIVENESS TO THERAPY

CROSS-REFERENCE TO RELATED APPLICATION

This application claims the benefit under 35 U.S.C. § 119(e) to U.S. Provisional Application No. 62/234,581, filed Sep. 29, 2015, the entire content of which is incorporated by reference into the present disclosure.

STATEMENT OF FEDERAL FUNDING

This application is a national stage entry under 35 U.S.C. § 371 of International Application No. PCT/US2016/054215, filed Sep. 28, 2016, which claims the benefit under 35 U.S.C. § 119(e) to U.S. Provisional Application No. 62/234,581, filed Sep. 29, 2015, the entire content of each of which is incorporated by reference into the present disclosure.

BACKGROUND

Chronic scarring, or "fibrosis", of the liver, lung, kidney, heart and other vital organ systems has no effective treatment, and is estimated to account for up to 45% of all deaths in the industrialized world. There are currently no FDA or EMEA-approved antifibrotic therapies.

Fibrosis is a common and debilitating pathology in many chronic liver diseases that hinders effective treatment and heightens the need for liver transplantation. Hepatic fibrosis is a common response to chronic injury and inflammation in the liver, resulting in excessive production and deposition of insoluble collagen and extracellular matrix components.

Affecting 5.5 million American adults (i.e. 2-3% of the adult U.S. population), hepatic fibrosis is a serious medical problem because it compromises normal hepatic structure and function and is a harbinger of cirrhosis, hepatocarcinoma, and end-stage liver disease. Liver fibrosis is most commonly seen in patients with chronic liver injury (hepatitis and alcohol abuse) although the pediatric population can be affected as well (biliary atresia, congenital). With the current explosion of obesity-related health problems such as fatty livers, a huge increase in the number of patients at risk for or who have developed liver fibrosis is to be expected. There are many other types of scarring that lack effective treatment. For example, dermal scarring and abdominal adhesions occur in a high proportion of the >42 million surgeries performed each year in the United States but, again there is no FDA-approved medication to prevent or reduce scars. This market alone is estimated at $4 billion.

Thus, a need exists for effective methods of detecting hepatic fibrosis. In addition, a needs exists for non-invasive detection of hepatic fibrosis and a needs exists for effective methods for determining whether a subject will be responsive to a fibrosis treatment. This disclosure satisfies these needs and provides related advantages as well.

SUMMARY

This disclosure provides methods for diagnosis of fibrosis, e.g., hepatic fibrosis, and determining responsiveness of hepatic fibrosis to therapy, each of which are unmet medical needs. As disclosed in more detail herein, this disclosure provides methods for determining whether a subject is suffering from a fibrotic or a liver disease, comprising determining the expression level of one or more miRNA listed in Table 1 and 2, in a sample of exosomes isolated from a body fluid of the subject, wherein differential expression of at least two fold or more of one or more miRNA as compared to a control is indicative of the subject suffering from a fibrotic disease or a liver disease. In one aspect, the exosomes of a subject suffering from a disease, e.g., a liver disease have a unique molecular profile in that the microRNA (miR or miRNA) profile of the exosomes comprises differential expression (e.g., at least two fold) as compared to the exosome miR profile of healthy control subject. In some embodiments, the liver disease is cirrhosis of the liver. In some embodiments, the subject is infected with the hepatitis B virus.

In one aspect, disclosed herein is a method of determining whether a subject has, or is more or less likely to suffer from a fibrotic disease, liver fibrosis or cirrhosis, comprising determining the expression level of one or more of the miRNAs listed in Table 1 in a sample of exosomes isolated from a body fluid of the subject, wherein differential expression of the one or more miRNA compared to control is indicative of the subject having, or more likely to suffer from a fibrotic disease, liver fibrosis or cirrhosis. In some embodiments, the method comprises determining the level of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, fifty-five or more of, or all of the miRNAs listed in Table 1 in the sample of exosomes.

Figure 1:
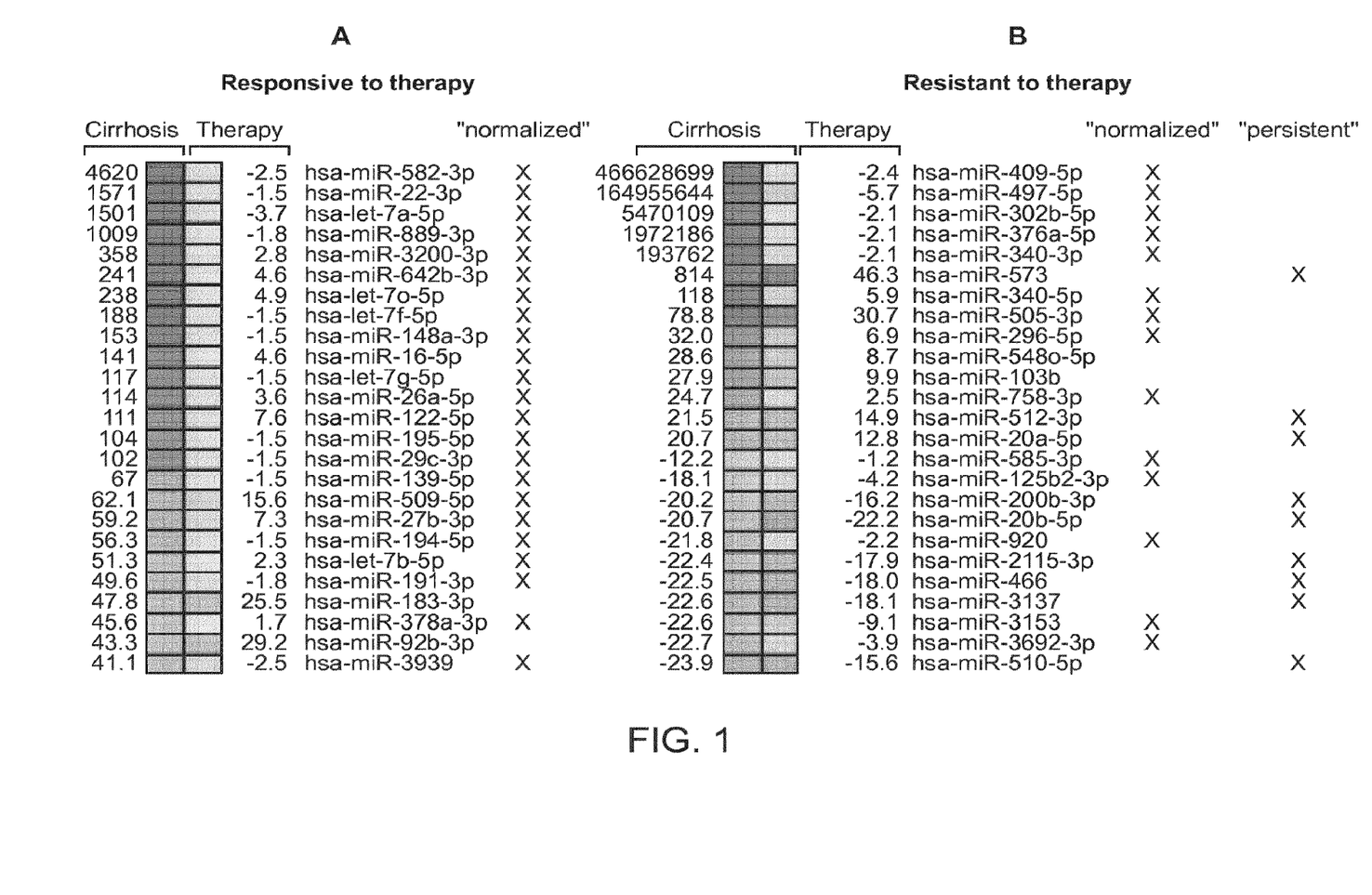
FIGS. 1A & 1B show heat maps depicting serum exosomal miRs with a ±15-fold expression change (range: +10,000-fold (dark grey)-to 1500-fold (light grey)) in cirrhosis patients as compared to healthy controls (left row) and the same serum exosomal miRs in the same patients after therapy (right row).

Further disclosed herein are methods of determining whether a subject suffering from a fibrotic disease or a liver disease is more or less likely to be responsive to a therapy to treat the disease, comprising determining the expression level of one or more miRNA listed in Table 1 and 2, in a sample of exosomes isolated from a body fluid of the subject, wherein differential expression of at least two fold or more of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p ["Normalized" in FIG. 1A] compared to a control indicates the subject is more likely to be responsive to therapy and/or wherein differential expression of at least two fold or more of one or more miRNA selected from: 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p ["Persistent" in FIG. 1B"] compared to a control indicates the subject is less likely to be responsive to the therapy. In some embodiments, differential expression of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p, of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being more likely to be responsive to the therapy. ["Normalized" in FIG. 1A]. In some embodiments, differential expression of one or more miRNA selected from: 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p, of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being likely to be non-responsive to the therapy. ["Persistent" in FIG. 1B"]

In some embodiments, the method comprises determining the expression level of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more or all of the miRNAs.

Disclosed herein, in some embodiments, is a method of determining whether a subject suffering from a fibrotic or a liver disease is more or less likely to experience reversal, comprising determining the expression level of one or more miRNA listed in Table 1 and 2, in a sample of exosomes isolated from a body fluid of the subject, wherein differential expression of at least two fold or more of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p ["Normalized" in FIG. 1A] compared to a control indicates the subject is more likely to experience reversal and/or wherein differential expression of at least two fold or more of one or more miRNA selected from: 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p ["Persistent" in FIG. 1B"] compared to a control indicates the subject is less likely to experience reversal. In some embodiments, the method comprises determining the expression level of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, or fifty-five or more of the miRNAs listed in Tables 1 and 2 in the sample of exosomes.

In some embodiments, the therapy for liver disease is selected from: cessation of alcohol consumption, weight loss, a low-sodium diet, or treatment with a medication selected from: antibiotics, anti-inflammatories, antivirals, immunosuppressives, diuretics, vitamins (A, D. E and K), drugs for metabolic diseases, and drugs to prevent ammonia accumulation. In some embodiments, the therapy is an antiviral medication selected from interferon alpha, pegylated interferon, lamivudine, adefovir dipivoxil, entecavir, telbivudine, and tenofovir.

In regards to the disclosed methods, in some embodiments, the subject is a mammal. In some embodiments, the subject is a human. In some embodiments, the subject is infected with a hepatitis B virus.

In regards to the disclosed methods, in some embodiments, the body fluid comprises one or more of blood, urine, saliva, breast milk, lymphatic fluid, serum and/or plasma. In some embodiments, the body fluid comprises urine. In some embodiments, the exosomes have an average diameter from about 10 to about 250 nm. In some embodiments, the exosomes are isolated by ultracentrifugation. In some embodiments, the exosomes are isolated from a biological sample using an exosome surface marker. In some embodiments, the exosomes are retained on a capture surface sufficient to retain the exosome fraction on or in the capture surface. In some embodiments, the capture surface is positively charged. In some embodiments, the capture surface is a membrane comprising regenerated cellulose or quaternary ammonium. In some embodiments, the exosomes are isolated using an exosome-specific antibody. In some embodiments, the antibody specifically binds to Rab 5b, HSPA8, CD9, GAPDH, ACTB, CD63, CD81, ANXA2, ENO1, HSP90AA1, EEF1A1, PKM2, YWHAE, SDCBP, PDCD61P, ALB, YWHAZ, EEF2, ACTG1, LDHA, HSP90AB1, ALDOA, MSN, ANXA5, PGK1, and CFL1. In some embodiments, the exosomes are isolated using size exclusion chromatography, filtration or immunosorbent capture. In some embodiments, the sample of exosomes comprises whole exosomes or an exosome lysate.

In regards to the disclosed methods, in some embodiments, said determining step comprises labeling the one or more miRNA with a detectable label.

In some embodiments, said determining step comprises capturing the one or more miRNA with one or more polynucleotide probe that selectively binds each of the one or more miRNA.

In some embodiments, said determining step comprises using a real-time polymerase chain reaction or a nucleic acid array.

In some embodiments, the disclosed methods further comprise the step of administering a therapeutic drug for the disease, e.g. fibrosis, a liver disease, a hepatic disease or an associated disorder.

In another aspect, further disclosed herein are kits comprising one or more probes and/or primers to determine the expression profile of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, or fifty-five or more of the miRNAs listed in Tables 1 and 2. In some embodiments, the kits comprise probes and/or primers to determine the expression profile of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, fifty-five or more or all of the miRNAs listed in Table 1. In a further aspect, the kits further contain instructions for sample isolation, and/or preparation and/or testing.

In some embodiments, the kits disclosed herein comprise probes and/or primers to determine the expression profile of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p. ["Normalized" in FIG. 1A]

In some embodiments, the kits disclosed herein comprise probes and/or primers to determine the expression profile of one or more miRNA selected from 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p. ["Persistent" in FIG. 1B"]

In regards to the kits disclosed herein, in some embodiments, the one or more probes and/or primers are detectably labeled. In some embodiments, the probes and/or primers are detectably labeled with an enzymatic, radioactive, fluorescent and/or luminescent moiety.

In some embodiments, the kits disclosed herein further comprise a purified or isolated population of exosomes isolated from a body fluid of a non-diseased subject, or nucleic acid isolated from said population of exosomes, as a negative control. In one aspect, the non-diseased subject is one who is identified as not having the corresponding disease, e.g., free of fibrosis or liver disease.

In some embodiments, the kits disclosed herein further comprise a purified or isolated population of exosomes isolated from a body fluid of a subject diagnosed with a fibrotic, a liver or hepatic disease or associated disorder, or nucleic acid isolated from said population of exosomes, as a positive control. In some embodiments, the subject diagnosed with a fibrotic disease, a liver or hepatic disease or associated disorder is resistant to a therapy for said disease or disorder. In some embodiments, the subject diagnosed with a fibrotic disease, a liver or hepatic disease or associated disorder is responsive to a therapy for said disease or disorder. In some embodiments, the therapy is cessation of alcohol consumption, weight loss, a low-sodium diet, or treatment with a medication selected from: antibiotics, anti-inflammatories, antivirals, immunosuppressives, diuretics, vitamins (A, D, E and K), drugs for metabolic diseases, and drugs to prevent ammonia accumulation. In some embodiments, the therapy is an antiviral medication selected from interferon alpha, pegylated interferon, lamivudine, adefovir dipivoxil, entecavir, telbivudine, and tenofovir.

BRIEF DESCRIPTION OF THE DRAWINGS

(FIG. 1A) Exosomal miRs in patients whose fibrosis was known to be improved after anti-viral therapy. The miRs in FIG. 1A will identify patients with cirrhosis. Of this panel, the miRs labeled as "normalized" represent fibrosis markers of patients whose fibrosis will diminish following anti-viral therapy; (FIG. 1B) Exosomal miRs in patients whose fibrosis was known NOT to be improved after anti-viral therapy. The miRs in FIG. 1B will identify cirrhosis. Of this panel, the miRs labeled as "persistent" (similar or worsened expression after therapy) represent markers of patients in whom it can be determined, either before or after anti-viral treatment, that they are resistant to fibrosis reversal. The numerical values depicted in FIGS. 1A-1B can be found in Tables 1 and 2 in the Examples.

DETAILED DESCRIPTION

Throughout this disclosure, various publications, patents and published patent specifications are referenced by an identifying citation. The disclosures of these publications, patents and published patent specifications are hereby incorporated by reference into the present disclosure to more fully describe the state of the art to which this disclosure pertains.

The practice of the present disclosure employs, unless otherwise indicated, techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, $3^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney $5^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

Definitions

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "exosome" intends a membrane body having an average diameter of from about 10 nm to about 2,000 nm. The term includes microvesicles and exosomes. Microvesicles are also known as circulating microvesicles or microparticles and are fragments of plasma membrane ranging from 100 nm to 1000 nm in approximate diameter shed from almost all cell types. For the purpose of this disclosure and unless specifically noted, the term exosome also includes smaller intracellularly generated extracellular vesicles formed by inward budding of the limiting membranes of multivesicular bodies (MVB) which, upon fusion with the plasma membrane, result in their secretion and deposition into body fluids (e.g., blood, urine). Exosomes contain a complex mixture of microRNAs (miRs), mRNAs and proteins that reflect the transcriptional and translational status of the producer cell. Exosomes are from about 10 to about 250 nm, or alternatively from about 10 to about 200 nm, or alternatively from about 10 to about 175 nm, or alternatively from about 25 to 175 nm, or alternatively from about 40 to about 250 nm, or alternatively from about 40 to about 200 nm, or alternatively from about 50 to 250 nm, or alternatively from about 50 to 200 nm, or alternatively from about 50-150 nm in average diameter. The exosome membranous vesicles arise by inward budding from the limiting membranes of MVB. Upon fusion of MVBs with the plasma membrane, exosomes are liberated from the cells, traverse intercellular spaces, and may be taken up by neighboring cells (Johnstone, R. M. (2006) Blood Cells Mol. Dis. 36(2):315-321; Thery, C. (2011) F1000 Biol. Rep. 3:15; Thery, C. et al. (2002) Nat. Rev. Immunol. 2(8):569-579). Exosomes contain a complex mixture of miRs, mRNAs and proteins and can be isolated from a variety of body fluids as described herein and known in the art.

As used herein, the term "fibrosis" intends the formation of an abnormal amount of insoluble scar tissue as the result of inflammation, irritation, or healing. It is a common and highly debilitating pathology and an end-stage manifestation of diseases such as systemic sclerosis, renal, pulmonary, or cardiac hypertension, myocardial infarction, and chronic liver disease (e.g., hepatitis, alcoholic liver disease, or non-alcoholic steatohepatitis). Numerous studies suggest that fibrosis in different organ systems share common mechanisms including inflammation, a prolonged wound healing response, activation of pro-fibrotic signals, increased matrix deposition and decreased matrix degradation, increased tissue stiffness, and loss of tissue elasticity. Collectively these changes in tissue architecture conspire to cause a loss of normal cell function and viability. Thus anti-fibrotic interventions will likely have utility for antagonizing fibrogenic pathways in a broad variety of fibrotic organ systems, or in tissues undergoing other types of scarring responses.

As used herein, the term "fibrotic disease or condition" intends a pathological condition having symptoms and clinical markers of fibrotic tissue, e.g., systemic sclerosis, renal, pulmonary, or cardiac hypertension, myocardial infarction, and chronic liver disease (e.g., hepatitis, alcoholic liver disease, or non-alcoholic steatohepatitis). Non-limiting examples of fibrotic conditions are provided in Table 3, below.

TABLE 3

ORGAN FIBROSIS

| Organ | Disorder | Cause | US Prevalance |
|---|---|---|---|
| Liver | Hepatic fibrosis/cirrhosis | Hepatitis A/B/C, alcoholic liver disease, non-alcoholic steatosis, biliary atresia, congenital | 400,000 |
| Heart | Cardiac fibrosis, cardiomyopathy | Aortic stenosis, emboli, hypertension | 100,000 |
| Kidney | End-stage renal disease | Diabetes, glomerulonephritis, hypertension | 250,000 |
| Lung | Pulmonary fibrosis, idiopathic pulmonary fibrosis | Environmental toxins, idiopathic | 150,000 |

TABLE 3-continued

| | | | |
|---|---|---|---|
| Pancreas | Chronic pancreatitis<br>Pancreatic<br>desmoplasia | Alcohol consumption,<br>episodic recurrent<br>acute pancreatitis<br>Pancreatic<br>adenocarcinoma | 175000 |
| Eye | Macular degeneration | Age-related, diabetes,<br>hypertension | 400,000 |

POST-SURGICAL FIBROSIS

| Surgical Procedure | US procedures/yr | Fibrosis |
|---|---|---|
| Tendon/peripheral nerve | 1,000,000 | Scarring within tendon sheaths and at nerve endings |
| Discectomy | 420,000 | Epidural fibrosis |
| Laminectomy | 400,000 | Peridural fibrosis |
| Arthroplasty | 650,000 | Peripatellar fibrosis |
| Cataract | 500,000 | Capsular fibrosis in 50% of patients |
| Glaucoma | 150,000 | Fibrosis closes the created fistula; 30% failure rate |
| Abdominal surgery | 1,000,000 | Abdominal adhesions, significant morbidity |
| Ob/Gyn surgery | 1,700,000 | Infertility secondary to scarring |
| Angioplasty | 400,000 | Fibrotic artery blockage (restenosis) in 40% of cases |
| Coronary bypass | 400,000 | Mediastinal fibrosis, Intimal fibrosis Endoluminal fibrosis |
| Organ transplant | 60,000 | Transplant failure |
| Plastic/revision surgery | 170000 | Scarring unavoidable |
| Dermal surgery | 42 million | Scarring of skin in most cases |

OTHER FORMS OF FIBROSIS

| Cause | US incidence | Cause |
|---|---|---|
| Scleroderma | 100,000 | Various, some unknown |
| Keloids | 300,000 | Skin trauma, genetic |
| Rheumatoid arthritis | 1.5 million | Fibrotic deposition in joint |
| Hypertrophic scars | 450,000 | Trauma/burns |
| Eye/corneal scars | 275,000 | Laser surgery, trauma, injury |

As used herein, "a non-diseased subject" intends a subject not diagnosed with a fibrotic disease. In one aspect, the non-diseased subject is one that does not have a clinical diagnosis of hepatic fibrosis and/or liver disease and/or has normal liver function. Clinical parameters for determining if a subject is suffering from a fibrotic disease are known in the art and briefly described herein. Without being limited, exemplary clinical tests for assessing liver function include: serum bilirubin test, serum alkaline phosphatase test, prothrombin time test, alanine transaminase test, aspartate transaminase test, gamma glutamyl transpeptidase test, lactate dehydrogenase test, alpha fetoprotein test, mitochondrial antibody test, and serum α-1 antitrypsin test. Clinical tests for detecting and diagnosing liver fibrosis include without limitation: PGA index, FIB-4 index, Fibrometer, FibroSure, Act-test, SAFE, Heapscore, FibroQ, AAR, APRI, CDS, API, Pohls score, Loks model, liver biopsy, ultrasonography, computed tomography, ultrasound elastography, and magnetic resonance elastography. For example, when the fibrotic condition is liver fibrosis, the above measurements can be combined with approved clinical tests for liver function and/or liver fibrosis.

The term "identify" or "identifying" is to associate or affiliate a patient closely to a group or population of patients who likely experience the same or a similar clinical response to treatment.

The terms "protein," "polypeptide" and "peptide" are used interchangeably herein when referring to a gene product.

The term "marker" refers to a clinical or sub-clinical expression of a gene or miRNA of interest.

"Expression" as applied to a gene, refers to the differential production of the miR or mRNA transcribed from the gene or the protein product encoded by the gene. A differentially expressed gene may be over expressed (high expression) or under expressed (low expression) as compared to the expression level of a normal or control cell, a given patient population or with an internal control gene (housekeeping gene). In one aspect, it refers to a differential that is about 1.5 times, or alternatively, about 2.0 times, alternatively, about 2.0 times, alternatively, about 3.0 times, or alternatively, about 5 times, or alternatively, about 10 times, alternatively about 50 times, or yet further alternatively more than about 100 times higher or lower than the expression level detected in a control sample.

In one aspect of the disclosure, a "predetermined threshold level" or "threshold value" is used to categorize expression as high or low. As a non-limiting example of the disclosure, the threshold level of the miR of the exosome is a level of miR expression found in subjects that have been diagnosed with a fibrotic or hepatic disease or an associate disorder. Alternatively or in addition, the predetermined threshold level is the measured miRNA expression level for that individual subject prior to a subsequent measurement, e.g., prior to therapy or prior to an additional dose of the therapy.

In one aspect of the disclosure, miR expression can be provided as a ratio above the threshold level and therefore can be categorized as high expression or up-regulated, whereas a ratio below the threshold level is categorized as down-regulated or low expression.

In another aspect, "expression" level is determined by measuring the expression level of a gene of interest for a given patient population, determining the median expression level of that gene for the population, and comparing the expression level of the same gene for a single patient to the median expression level for the given patient population. For example, if the expression level of a gene of interest for the single patient is determined to be above the median expression level of the patient population, that patient is determined to have high expression (up-regulated) of the gene of interest. Alternatively, if the expression level of a gene of interest for the single patient is determined to be below the median expression level (down-regulated) of the patient population, that patient is determined to have low expression of the gene of interest.

A "internal control" or "housekeeping" gene refers to any constitutively or globally expressed gene whose presence enables an assessment of the expression level of a gene or genes of interest. Such an assessment comprises a determination of the overall constitutive level of gene transcription and a control for variation in sampling error. Examples of such genes include, but are not limited to, RNU6-2, cel-miR-39, SNORD61, SNORD68, SNORD72, SNORD95, SNORD96A, GADPH and/or β-actin.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The phrase "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Innis et al., 1990 (for PCR); and Wu, D. Y. et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e., each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed from its gene and/or translated from its mRNA to produce the polypeptide and/or a fragment thereof. The antisense strand is the complement of such a nucleic acid, and the encoding sequence can be deduced therefrom.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

A "blood cell" refers to any of the cells contained in blood. A blood cell is also referred to as an erythrocyte or leukocyte, or a blood corpuscle. Non-limiting examples of blood cells include white blood cells, red blood cells, and platelets.

"Expression" as applied to a gene, refers to the production of the miR or mRNA transcribed from the gene, or the protein product encoded by the mRNA. The expression level of a gene may be determined by measuring the amount of miR or mRNA or protein in a cell or tissue sample. In one aspect, the expression level of a gene is represented by a relative level as compared to a housekeeping gene as an internal control. In another aspect, the expression level of a gene from one sample may be directly compared to the expression level of that gene from a different sample using an internal control to remove the sampling error.

"Differential expression," "overexpression" or "underexpression" refers to increased or decreased expression, or alternatively a differential expression, of a gene in a test sample as compared to the expression level of that gene in the control sample. In one aspect, the test sample is a diseased cell, and the control sample is a normal cell. In another aspect, the test sample is an experimentally manipulated or biologically altered cell, and the control sample is the cell prior to the experimental manipulation or biological alteration. In yet another aspect, the test sample is a sample from a patient, and the control sample is a similar sample from a healthy individual. In a yet further aspect, the test sample is a sample from a patient and the control sample is a similar sample from patient not having the desired clinical outcome. In one aspect, the differential expression is about 1.5 times, or alternatively, about 2.0 times, or alternatively, about 2.0 times, or alternatively, about 3.0 times, or alternatively, about 5 times, or alternatively, about 10 times, or alternatively about 50 times, or yet further alternatively more than about 100 times higher or lower than the expression level detected in the control sample. Alternatively, the gene is referred to as "over expressed" or "under expressed". Alternatively, the gene may also be referred to as "up regulated" or "down regulated".

A "predetermined value" for a gene as used herein, is so chosen that a patient with an expression level of that gene higher than the predetermined value is likely to experience a more or less desirable clinical outcome than patients with expression levels of the same gene lower than the predetermined value, or vice-versa. Expression levels of genes, such as those disclosed in the present disclosure, are associated with clinical outcomes. One of skill in the art can determine a predetermined value for a gene by comparing expression levels of a gene in patients with more desirable clinical outcomes to those with less desirable clinical outcomes. In one aspect, a predetermined value is a gene expression value that best separates patients into a group with more desirable clinical outcomes and a group with less desirable clinical outcomes. Such a gene expression value can be mathematically or statistically determined with methods well known in the art.

Alternatively, a gene expression that is higher than the predetermined value is simply referred to as a "high expression", or a gene expression that is lower than the predetermined value is simply referred to as a "low expression".

Briefly and for the purpose of illustration only, one of skill in the art can determine a predetermined values by comparing expression values of a gene in patients with more desirable clinical parameters to those with less desirable clinical parameters. In one aspect, a predetermined value is a gene expression value that best separates patients into a group with more desirable clinical parameter and a group with less desirable clinical parameter. Such a gene expression value can be mathematically or statistically determined with methods well known in the art.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine," "cytidine," "guanosine," and "thymidine" are used. It is understood that if the nucleic acid is RNA, a nucleotide having a uracil base is uridine.

The terms "oligonucleotide" or "polynucleotide," or "portion," or "segment" thereof refer to a stretch of polynucleotide residues which is long enough to use in PCR or various hybridization procedures to identify or amplify identical or related parts of miR or mRNA or DNA molecules. The polynucleotide compositions of this disclosure include miR, RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

microRNAs, miRNAs, or miRs are single-stranded RNA molecules of 19-25 nucleotides in length, which regulate gene expression. miRNAs are encoded by genes from whose DNA they are transcribed but miRNAs are not translated into protein (non-coding RNA); instead each primary transcript (a pri-miRNA) is processed into a short stem-loop structure called a pre-miRNA and finally into a functional miRNA. Mature miRNA molecules are partially complementary to one or more messenger RNA (mRNA) molecules, and their main function is to down-regulate gene expression.

When a marker is used as a basis for selecting a patient for a treatment described herein, the marker is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker or polymorphism in a clinical setting is a clear indication that this parameter was used as a basis for initiating, continuing, adjusting and/or ceasing administration of the treatments described herein.

The term "treating" as used herein is intended to encompass curing as well as ameliorating at least one symptom of the condition or disease. For example, in the case of liver fibrosis, the term "treatment" intends a more favorable clinical assessment by a treating physician or assistant and/or reduced expression of fibrosis markers, e.g., αSMA, CTGF, collagen, matrix molecules and/or a shift toward normal read-outs in tests that diagnose liver function and/or liver fibrosis.

"An effective amount" intends to indicated the amount of a composition, compound or agent (exosomes) administered or delivered to the subject that is most likely to result in the desired response to treatment. The amount is empirically determined by the patient's clinical parameters including, but not limited to the stage of disease, age, gender and histology.

The term "blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood.

A "composition" is intended to mean a combination of active exosome or population of exosomes and another compound or composition, inert (e.g., a detectable label or saline) or active (e.g., a therapeutic compound or composition) alone or in combination with a carrier which can in one embodiment be a simple carrier like saline or pharmaceutically acceptable or a solid support as defined below.

A "pharmaceutical composition" is intended to include the combination of an active exosome or population of exosomes with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, the disease being treated and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application.

An agent of the present disclosure can be administered for therapy by any suitable route of administration. It will also be appreciated that the preferred route will vary with the condition and age of the recipient, and the disease being treated.

Diagnostic Methods

This disclosure provides diagnostic methods. In one aspect, therapy and a subject's health can be monitored by determining the expression level of one or more miRs listed in Tables 1 and 2 in a sample of exosomes isolated from the subject prior to, during, and/or after the therapy. The method can further comprise, or alternatively consist essentially of, or yet further consist of, determining the expression level of one or more of, two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, fifty-five or more of, or all of the miRNAs listed in Table 1 and 2 in a sample of exosomes isolated from the subject.

The methods are useful in the diagnosis of a subject, e.g., a mammal, an animal, or yet further a human patient. For the purpose of illustration only, a mammal includes but is not limited to a human, a simian, a murine, a rat, a bovine, a canine, a feline, an equine, a porcine or an ovine.

In some embodiments, disclosed herein are methods for determining whether a subject is suffering from a fibrotic or a liver disease, comprising determining the expression level of one or more miRNA listed in Table 1 and 2, in a sample of exosomes isolated from a body fluid of the subject, wherein differential expression of at least two fold or more of one or more miRNA as compared to a control is indicative of the subject suffering from a fibrotic or a liver disease. In some embodiments, the liver disease is cirrhosis of the liver. In some embodiments, the subject is infected with the hepatitis B virus.

In one aspect, disclosed herein is a method of determining whether a subject has, or is more or less likely to suffer from a fibrotic disease, e.g., liver cirrhosis, comprising determining the expression level of one or more of the miRNAs listed in Table 1 in a sample of exosomes isolated from a body fluid of the subject, wherein differential expression of the one or more miRNA compared to control is indicative of the subject having, or more likely to suffer from the disease.

Further disclosed herein are methods of determining whether a subject suffering from a fibrotic or a liver disease is more or less likely to be responsive to a therapy to treat the disease, comprising determining the expression level of one or more miRNA listed in Table 1 and 2, in a sample of exosomes isolated from a body fluid of the subject, wherein differential expression of at least two fold or more of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p ["Normalized" in FIG. 1A] compared to a control indicates the subject is more likely to be responsive to therapy and/or wherein differential expression of at least two fold or more of one or more miRNA selected from: 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p ["Persistent" in FIG. 1B"] compared to a control indicates the subject is less likely to be responsive to the therapy.

In some embodiments, differential expression of one or more of the disclosed miRNAs of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being more likely to be responsive to the therapy.

In some embodiments, differential expression of one or more of the disclosed miRNAs of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being likely to be non-responsive to the therapy.

Disclosed herein, in some embodiments, is a method of determining whether a subject suffering from a fibrotic disease or a liver disease is more or less likely to experience reversal, e.g., fibrotic or liver disease reversal, comprising determining the expression level of one or more miRNA listed in Table 1 and 2, in a sample of exosomes isolated from a body fluid of the subject, wherein differential expression of at least two fold or more of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p ["Normalized" in FIG. 1A] compared to a control indicates the subject is more likely to experience reversal and/or wherein differential expression of at least two fold or more of one or more miRNA selected from: 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p ["Persistent" in FIG. 1B"] compared to a control indicates the subject is less likely to experience reversal.

In some embodiments, differential expression of one or more of the disclosed miRNAs of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being more likely to experience fibrosis or liver disease reversal.

In some embodiments, differential expression of one or more of the disclosed miRNAs of at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control is indicative of the subject being likely to experience fibrosis or liver disease reversal.

In regards to the disclosed methods, in some embodiments, the subject is a mammal. In some embodiments, the subject is a human. In some embodiments, the subject is infected with a hepatitis B virus.

In some embodiments, the therapy for fibrosis or liver disease is selected from, but not limited to: cessation of alcohol consumption, weight loss, a low-sodium diet, or treatment with a medication selected from: antibiotics, anti-inflammatories, antivirals, immunosuppressives, diuretics, vitamins (A, D, E and K), drugs for metabolic diseases, and drugs to prevent ammonia accumulation. In some embodeiments, the therapy is an antiviral medication selected from interferon alpha, pegylated interferon, lamivudine, adefovir dipivoxil, entecavir, telbivudine, and tenofovir.

Collection of body fluid samples, e.g., urine, blood, saliva, breast milk, lymphatic fluid, serum or plasma, for exosome miR analysis, can be done with methods known in the art.

In some embodiments, the exosomes are isolated from the sample prior to determination of the miR profile. The exosomes can be purified from the fluid using the methods disclosed herein in art-recognized methods, such as by ultracentrifugation as described by Thery et al. (2006) "Isolation and characterization of exosomes from cell culture supernatants and biological fluids" Curr. Protoc. Cell Biol., Chapter 3, or as disclosed in Hong et al. (2014) PLoS One 9(8):e103310, doe:10,1371 and Jayachandran et al. (2012) J. Immun. Methods, 375:207-214. Commercial kits also are available, e.g., PureExo (101BIO, Palo Alto Calif., for serum and plasma), Exo MIR Plus (Bioo Scientific, Austin Tex., USA), ExoQuick (SBI, Mountain View, Calif., USA, for tissue culture) and Exo-Spin Kit (Cell Guidance Systems, Carlsbad Calif., USA). As apparent to the skilled artisan, the isolation method will depend on the size and composition of the exosome to be isolated As an example, ultracentrifugation can be used but for larger microvesicles, and the speed shall not exceed about 70,000g or alternatively about 60,000g. Alternatively, ultracentrifugation is used for smaller exosomes, but being much smaller, speeds of 90,000 or alternatively of 100,000g or more are needed. In some embodiments, the exosomes are isolated by ultracentrifugation. In some embodiments, the exosomes are isolated from a biological sample using an exosome surface marker. In some embodiments, the exosomes are retained on a capture surface sufficient to retain the exosome fraction on or in the capture surface. In some embodiments, the capture surface is positively charged. In some embodiments, the capture surface is a membrane comprising regenerated cellulose or quaternary ammonium. In some embodiments, the exosomes are isolated using an exosome-specific antibody. In some embodiments, the antibody specifically binds to Rab 5b, HSPA8, CD9, GAPDH, ACTB, CD63, CD81, ANXA2, ENO1, HSP90AA1, EEF1A1, PKM2, YWHAE, SDCBP, PDCD61P, ALB, YWHAZ, EEF2, ACTG1, LDHA, HSP90AB1, ALDOA, MSN, ANXA5, PGK1, and CFL1. In some embodiments, the exosomes are isolated using size exclusion chromatography, filtration or immunosorbent capture.

In one aspect, the exosomes have an average diameter from about 10 to about 250 nm, or alternatively from about 10 to about 200 nm, or alternatively from about 10 to about 175 nm, or alternatively from about 25 to 175 nm, or alternatively from about 40 to about 250 nm, or alternatively from about 40 to about 200 nm, or alternatively from about 50 to 250 nm, or alternatively from about 50 to 200 nm, or alternatively from about 50-150 nm in average diameter. In another aspect, the term exosome also includes microvesicles that range from 100 nm to 1000 nm in approximate diameter.

In some embodiments, the analyzed sample of exosomes comprises whole exosomes or an exosome lysate.

Measurement of expression level or activity level can be accomplished by methods known in the art and briefly described herein, e.g., by PCR. The measurement can be compared to suitable controls, e.g., a prior measurement for that subject or a suitable internal control.

In regards to the disclosed methods, in some embodiments, said determining step comprises labeling the one or more miRNA with a detectable label.

In some embodiments, said determining step comprises capturing the one or more miRNA with one or more polynucleotide probe that selectively binds each of the one or more miRNA.

In some embodiments, said determining step comprises using a real-time polymerase chain reaction or a nucleic acid array.

In some embodiments, the disclosed methods further comprise the step of administering a therapeutic drug for the fibrotic, the hepatic disease or an associated disorder. In some embodiments, the therapeutic drug is selected from: antibiotics, anti-inflammatories, antivirals, immunosuppressives, diuretics, vitamins (A, D, E and K), drugs for metabolic diseases, and drugs to prevent ammonia accumulation. In some embodiments, the therapeutic drug is an antiviral medication selected from interferon alpha, pegylated interferon, lamivudine, adefovir dipivoxil, entecavir, telbivudine, and tenofovir. In some embodiments, the therapeutic drug is a purified or isolated population of exosomes isolated from a body fluid of a non-diseased subject.

The measurement of the above-noted miRNA markers can be combined with clinical parameters. Without being limited, exemplary clinical tests for assessing liver function include: serum bilirubin test, serum alkaline phosphatase test, prothrombin time test, alanine transaminase test, aspartate transaminase test, gamma glutamyl transpeptidase test, lactate dehydrogenase test, alpha fetoprotein test, mitochondrial antibody test, and serum a-1 antitrypsin test. Clinical tests for detecting and diagnosing liver fibrosis include without limitation: PGA index, FIB-4 index, Fibrometer, FibroSure, Act-test, SAFE, Heapscore, FibroQ, AAR, APRI, CDS, API, Pohls score, Loks model, liver biopsy, ultrasonography, computed tomography, ultrasound elastography, and magnetic resonance elastography. For example, when the fibrotic condition is liver fibrosis, the above measurements can be combined with approved clinical tests for liver function and/or liver fibrosis.

In another aspect, further disclosed herein are kits comprising one or more probes and/or primers to determine the expression profile of one or more of two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, or fifty-five or more of the miRNAs listed in Tables 1 and 2. In some embodiments, the kits comprise probes and/or primers to determine the expression profile of one or more of two or more, three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, thirty-five or more, forty or more, forty-five or more, fifty or more, fifty-five or more or all of the miRNAs listed in Table 1.

In some embodiments, the kits disclosed herein comprise probes and/or primers to determine the expression profile of one or more miRNA selected from: 582-3p, 22-3p, let-7a-5p, 889-3p, 3200-3p, 642b-3p, let-7c-5p, let-7f-5p, 148s-3p, 16-5p, let-7g-5p, 26a-5p, 122-5p, 195-5p, 29c-3p, 139-5p, 509-5p, 27b-3p, 194-5p, let-7b-5p, 191-3p, 378a-3p, 3939, 2114-3p, 188-3p, 106b-30, 942-5p, 632, 370-3p, 566, 15b-5p, 548d-3p, 147a, 7-1-3p, 936, 551b-5p, 3679-5p, 616-3p, 668-3p, 7-2-3p, 196a-3p, 538b-5p, 34b-3p, 892a, and 500a-5p. ["Normalized" in FIG. 1A]

In some embodiments, the kits disclosed herein comprise probes and/or primers to determine the expression profile of one or more miRNA selected from 573, 512-3p, 20a-5p, 200b-3p, 20b-5p, 2115-3p, 466, 3137, 510-5p, 4267, 515-3p, 24-2-5p, 3117-3p, 668-3p, 132-3p, let-7e-5p, 3074-3p, 4260, 4288, 936, 4254, 148b-3p, 378b, 2909, and 193a-5p. ["Persistent" in FIG. 1B"]

In regards to the kits disclosed herein, in some embodiments, the one or more probes and/or primers are detectably labeled. In a further aspect, the kit further comprises detectable labels that in one aspect are attached to the probes and/or primers, wherein in one aspect, the detectable label is not a polynucleotide. In some embodiments, the probes and/or primers are detectably labeled with an enzymatic, radioactive, fluorescent and/or luminescent moiety. In one aspect, the detectable label is not a polynucleotide that is naturally fluorescent or detectable.

In some embodiments, the kits disclosed herein further comprise a purified or isolated population of exosomes isolated from a body fluid of a non-diseased subject, or nucleic acid isolated from said population of exosomes, as a negative control.

In some embodiments, the kits disclosed herein further comprise a purified or isolated population of exosomes isolated from a body fluid of a subject diagnosed with a fibrotice, liver or hepatic disease or associated disorder, or nucleic acid isolated from said population of exosomes, as a positive control. In some embodiments, the subject diagnosed with a fibrotic, liver or hepatic disease or associated disorder is resistant to a therapy for said disease or disorder. In some embodiments, the subject diagnosed with a fibrotic, a liver or hepatic disease or associated disorder is responsive to a therapy for said disease or disorder.

The following examples are intended to illustrate, and not limit, the disclosed herein. For example, while the examples are noted to be for the isolation, purification and use of exosome compositions for the treatment of a fibrotic or liver disease or an associated disorder, the methods and compositions can be modified for the treatment of other fibrotic diseases as noted herein.

EXAMPLES

Example 1. Treatment and Regression of HBV-Induced Liver Fibrosis

Our analysis involved the study of patients who were enrolled in NCT01938781 (Optimized Treatment and Regression of HBV-induced Liver Fibrosis). In this interventional, randomized, open label study, chronic hepatitis B (CHB) patients (18-65 years of age, male or female, treatment-naïve) provided written consent and were randomly assigned to receive either (a) entecavir (ETV; an anti-viral drug for hepatitis B virus (HBV);) alone for 2 years or (b) ETV for the first ½ year, ETV+plus pegylated interferon (PEGSYS) for 1 year, and ETV for the last ½ year. Patients were assessed prior to treatment and at every six months for blood count, liver function tests (LFTs), HBV DNA, alpha-fetoprotein, prothrombin time, thyroid function, liver ultrasonography, and transient elastography (Fibroscan®). The primary objective was to establish the regression rate of HBV-induced liver fibrosis as assessed by liver biopsies, performed prior to treatment and at 1½ years after initial therapy. Secondary objectives included the HBV DNA non-detectable rate, HBe and HBs antigen seroconversion, and Fibroscan scores after 1- and 2-years of treatment. Inclusion criteria were: age ≥18 years, diagnosis of CHB (HBsAg positive for more than 6 months), and detectable HBV DNA (>1000 copies/ml). Exclusion criteria were co-infection with HCV or HIV, liver disease other than due to HBV, decompensated liver disease, organ transplantation, autoimmune disorders, consumption of >20g/day alcohol, and past history of intravenous drug use.

In the first analysis, twelve HBV patients with compensated cirrhosis were selected based on their known fibrosis regression (decreased Fibroscan values of >5 kPa) after treatment for 6 months with Entecavir (5 mg/day oral). Twelve matched healthy blood donors were used as a reference control group. Serum (0.5 ml) from the HBV patients, before or after therapy, or from the controls was individually processed to purify exosomes from which small RNA was then isolated. RNA quality was verified and reverse-transcribed with miRScriptRTII. Samples in each group were pooled and analyzed using a Human miRNome PCR array to profile the 1066 most abundantly expressed human miR sequences using SYBR Green real time PCR. Fold change values were calculated for each feature on the array. Genes with ≥+2-fold change were considered differentially expressed (Table 1). This unbiased analysis revealed that, compared to control subjects, 59 out of 1066 miRs were up- or down-regulated at least 15-fold in the cirrhotic patients, indicating that these 59 miRs are markers of HBV cirrhosis. Further, 46 out of 59 miRs showed correction (to levels closer to that of healthy controls samples) after therapy (FIG. 1A). Among the 59 miRs identified as being cirrhosis-related were miR-7, -15b, -16, -22, -26a, -27b, -29, -92b, -101, -183, -191, -196a, -200a, -370, -378a and -936 and let-7a,b,c,d,e,f,g, 19 of which showed corrected expression after therapy.

TABLE 1

Differential Expression of small RNAs in Patients with HBV Cirrhosis Responsive to Therapy (Values Depicted in FIG. 1A, numerical values are fold change in expression as compared to healthy control individuals)

| | Cirrhosis | Therapy | "Normalized" |
|---|---|---|---|
| hsa-miR-582-3p | 4620 | −2.5 | X |
| hsa-miR-22-3p | 1571 | −1.5 | X |
| hsa-let-7a-5p | 1501 | −3.7 | X |
| hsa-miR-889-3p | 1009 | −1.8 | X |
| hsa-miR-3200-3p | 358 | 2.8 | X |
| hsa-miR-642b-3p | 241 | 4.6 | X |
| hsa-let-7c-5p | 238 | 4.9 | X |
| hsa-let-7f-5p | 188 | −1.5 | X |
| hsa-miR-148a-3p | 153 | −1.5 | X |
| hsa-miR-16-5p | 141 | 4.6 | X |
| hsa-let-7g-5p | 117 | −1.5 | X |
| hsa-miR-26a-5p | 114 | 3.6 | X |
| hsa-miR-122-5p | 111 | 7.6 | X |
| hsa-miR-195-5p | 104 | −1.5 | X |
| hsa-miR-29c-3p | 102 | −1.5 | X |
| hsa-miR-139-5p | 67 | −1.5 | X |
| hsa-miR-509-5p | 62.1 | 15.6 | X |
| hsa-miR-27b-3p | 59.2 | 7.3 | X |
| hsa-miR-194-5p | 56.3 | −1.5 | X |
| hsa-let-7b-5p | 51.3 | 2.3 | X |
| hsa-miR-191-3p | 49.6 | −1.8 | X |
| hsa-miR-183-3p | 47.8 | 25.5 | |
| hsa-miR-378a-3p | 45.6 | 1.7 | X |
| hsa-miR-92b-3p | 43.3 | 29.2 | X |
| hsa-miR-3939 | 41.1 | −2.5 | X |

TABLE 1-continued

Differential Expression of small RNAs in Patients with HBV Cirrhosis Responsive to Therapy (Values Depicted in FIG. 1A, numerical values are fold change in expression as compared to healthy control individuals)

| | Cirrhosis | Therapy | "Normalized" |
|---|---|---|---|
| hsa-miR-4326 | 41.1 | 7.5 | |
| hsa-miR-2114-3p | 36.1 | 1.8 | X |
| hsa-miR-188-3p | 34.1 | −1.5 | X |
| hsa-miR-200a-5p | 31.1 | 8.8 | |
| hsa-miR-106b-3p | 29.1 | 2.4 | X |
| hsa-miR-942-5p | 28.9 | 1.7 | X |
| hsa-miR-186-3p | 28.2 | 6.4 | |
| hsa-miR-632 | 26.7 | 3.8 | X |
| hsa-let-7d-5p | 26.6 | −13.3 | |
| hsa-miR-4294 | 25.5 | 6.2 | |
| hsa-miR-370-3p | 25.3 | 1.8 | X |
| hsa-miR-101-3p | 24.5 | 8.9 | |
| hsa-miR-566 | 23.9 | 1.2 | X |
| hsa-miR-15b-5p | 23.8 | −1.5 | X |
| hsa-let-7e-5p | 20.9 | −8.3 | |
| hsa-miR-548d-3p | 20.2 | −1.5 | X |
| hsa-miR-147a | 20.1 | −1.5 | X |
| hsa-miR-7-1-3p | −14.8 | −6.2 | X |
| hsa-miR-936 | −15.9 | −4.4 | X |
| hsa-miR-551b-5p | −17.3 | −4.0 | X |
| hsa-miR-3679-5p | −18.7 | −12.7 | X |
| hsa-miR-616-3p | −20.0 | −13.7 | X |
| hsa-miR-3916 | −21.2 | −25.9 | |
| hsa-miR-668-3p | −22.1 | −9.6 | X |
| hsa-miR-3655 | −26.0 | −31.7 | |
| hsa-miR-7-2-3p | −27.8 | −4.5 | X |
| hsa-miR-196a-3p | −28.0 | −21.5 | X |
| hsa-miR-3147 | −32.3 | −31.2 | |
| hsa-miR-548b-5p | −32.7 | 9.8 | X |
| hsa-miR-3161 | −34.9 | −83.8 | |
| hsa-miR-34b-3p | −36.7 | −10.4 | X |
| hsa-miR-892a | −37.2 | −6.1 | X |
| hsa-miR-500a-5p | −43.9 | −10.6 | X |
| hsa-miR-2276-3p | −45.5 | −108.9 | |

In the second analysis, twelve HBV patients with compensated cirrhosis were selected based on their known lack of fibrosis regression after treatment for 6 mo with Entecavir (0.5 mg/day oral) and same analysis was performed as described above. As shown in FIG. 1B, these patients exhibited a different set of altered (+/−15-fold verus controls) miRs which define cirrhosis in this this cohort of non-responsive patients. These were overall different to those shown in FIG. 1A. 32 out of 59 of these miRs were more normalized following anti-viral therapy but since these patients' fibrosis was non-responsive to therapy, these 32 miRs are not markers of fibrosis. On the other hand, 25 miRs persisted at the same or exaggerated levels after therapy and thus are correlated—and markers of—the persistence of fibrosis.

TABLE 2

Differential Expression of small RNAs in Patients with HBV Cirrhosis Non-Responsive to Therapy (Values Depleted in FIG. 1B, numerical values are fold change in expression as compared to healthy control individuals)

| | Cirrhosis | Therapy | "Persistent" |
|---|---|---|---|
| hsa-miR-409-5p | 466628699 | −2.4 | |
| hsa-miR-497-5p | 164955644 | −5.7 | |
| hsa-miR-302b-5p | 5470109 | −2.1 | |
| hsa-miR-376a-5p | 1972186 | −2.1 | |
| hsa-miR-340-3p | 193762 | −2.1 | |
| hsa-miR-573 | 814 | 46.3 | X |
| hsa-miR-340-5p | 118 | 5.9 | |
| hsa-miR-505-3p | 78.8 | 30.7 | |

TABLE 2-continued

Differential Expression of small RNAs in Patients with
HBV Cirrhosis Non-Responsive to Therapy (Values Depleted
in FIG. 1B, numerical values are fold change in expression
as compared to healthy control individuals)

| | Cirrhosis | Therapy | "Persistent" |
|---|---|---|---|
| hsa-miR-296-5p | 32.0 | 6.9 | |
| hsa-miR-548o-5p | 28.6 | 8.7 | |
| hsa-miR-103b | 27.9 | 9.9 | |
| hsa-miR-758-3p | 24.7 | 2.5 | |
| hsa-miR-512-3p | 21.5 | 14.9 | X |
| hsa-miR-20a-5p | 20.7 | 12.8 | X |
| hsa-miR-585-3p | −12.2 | −1.2 | |
| hsa-miR-125b-2-3p | −18.1 | −4.2 | |
| hsa-miR-200b-3p | −20.2 | −16.2 | X |
| hsa-miR-20b-5p | −20.7 | −22.2 | X |
| hsa-miR-920 | −21.8 | −2.2 | |
| hsa-miR-2115-3p | −22.4 | −17.9 | X |
| hsa-miR-466 | −22.5 | −18.0 | X |
| hsa-miR-3137 | −22.6 | −18.1 | X |
| hsa-miR-3153 | −22.6 | −9.1 | |
| hsa-miR-3692-3p | −22.7 | −3.9 | |
| hsa-miR-510-5p | −23.9 | −15.6 | X |
| hsa-miR-100-5p | −24.1 | −1.1 | |
| hsa-miR-4267 | −24.1 | −13.5 | X |
| hsa-miR-1299 | −24.5 | −3.9 | |
| hsa-miR-320d | −25.1 | −8.3 | |
| hsa-miR-3678-5p | −25.3 | −3.2 | |
| hsa-miR-515-3p | −25.6 | −27.4 | X |
| hsa-miR-24-2-5p | −26.2 | −17.1 | X |
| hsa-miR-3117-3p | −26.2 | −16.2 | X |
| hsa-miR-193b-5p | −27.0 | −1.4 | |
| hsa-miR-3622a-5p | −27.1 | −6.6 | |
| hsa-miR-493-3p | −27.3 | −1.6 | |
| hsa-miR-668-3p | −27.5 | −76.5 | X |
| hsa-miR-1303 | −28.0 | −3.2 | |
| hsa-miR-675-5p | −28.6 | −6.2 | |
| hsa-miR-132-3p | −28.8 | −30.8 | X |
| hsa-let-7e-5p | −28.8 | −30.8 | X |
| hsa-miR-4290 | −28.8 | −2.5 | |
| hsa-miR-3074-3p | −28.9 | −34.4 | X |
| hsa-miR-639 | −30.2 | −8.1 | |
| hsa-miR-4260 | −30.9 | −468 | X |
| hsa-miR-3622b-3p | −32.4 | −3.1 | |
| hsa-miR-4288 | −32.5 | −26.1 | X |
| hsa-miR-936 | −33.5 | −21.9 | X |
| hsa-miR-3147 | −33.5 | −8.3 | |
| hsa-miR-4254 | −33.9 | −27.2 | X |
| hsa-miR-148b-3p | −34.0 | −36.4 | X |
| hsa-miR-378b | −34.0 | −61.7 | X |
| hsa-miR-3138 | −34.7 | −4.5 | |
| hsa-miR-4325 | −34.9 | −6.7 | |
| hsa-miR-2909 | −35.6 | −28.6 | X |
| hsa-miR-600 | −36.8 | 4.9 | |
| hsa-miR-193a-5p | −38.9 | −28.5 | X |
| hsa-miR-3149 | −39.7 | −14.3 | |
| hsa-miR-891a-5p | −40.8 | −2.6 | |

Thus, this data discloses the following:
1. miRs shown in the left column of FIG. 1A which define cirrhosis AND which are characteristic of patients who will respond to therapy ("Normalized")
2. Part or all of the miRs shown in the left column of FIG. 1B which define cirrhosis AND which are characteristic of patients who will not respond to therapy ("Persistent")
3. Part or all of the mIRs in the right column of FIG. 1A which are diagnostic of fibrosis reversal ("Normalized")
4. Part or all of the "persistent: mIRs in the right column of FIG. 1B which are diagnostic for patients in whom fibrosis will not be reversed after therapy ("Persistent")
5. Assignment of patients as responders or non-responders by determining if part or all of their mIR profile is more similar to that shown in the left column of FIG. 1A as compared to the left column of FIG. 1B.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The disclosures illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

What is claimed is:

1. A method of treating a subject suffering from an hepatitis B (HBV) induced liver fibrosis, comprising administering an antiviral drug for HBV to the subject selected by a method comprising determining differential expression of at least two fold or more of microRNA(miR)-582-3p and miR-22-3p in a sample of exosomes isolated from a body fluid of the subject compared to a control.

2. The method of claim 1, wherein the sample of exosomes further comprises a differential expression of one or more of: miR-let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-36'79-5p, miR-616-3p, miR-668-3p, miR-7-2-3p, miR-196a-3p, miR-538b-5p, miR-34b-3p, miR-892a, or miR-500a-5p, of at least 2 fold, at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control.

3. The method of claim 1, further comprising determining the expression level of one or more, or two or more, or three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or twenty-five or more, or twenty-six, or twenty-seven or more, or twenty-eight or more, or twenty-nine or more, or thirty or more, or thirty-five or more, or forty or more, or forty-five or more of miR-582-3p, miR-22-3p, let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-3679-5p, miR-616-3p, miR-668-3p, miR-7-2-3p, miR-196a-3p, miR-538b-5p, miR-34b-3p, miR-892a, or miR-500a-5p in the sample of exosomes.

4. The method of claim 1, wherein the sample of exosomes lacks a differential expression of one or more: miR-573, miR-512-3p, miR-20a-5p, miR-200b-3p, miR-20b-5p, miR-2115-3p, miR-466, miR-3137, miR-510-5p, miR-4267, miR-515-3p, miR-24-2-5p, miR-3117-3p, miR-668-3p, miR-132-3p, let-7e-5p, miR-3074-3p, miR-4260, miR-4288, miR-936, miR-4254, miR-148b-3p, miR-378b, miR-2909, or miR-193a-5p, of at least 2 fold, at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control.

5. The method of claim 4, further comprising determining the expression level of one or more, or two or more, or three or more, or four or more, or five or more, or six or more, or seven or more, or eight or more, or nine or more, or ten or more, or eleven or more, or twelve or more, or thirteen or more, or fourteen or more, or fifteen or more, or sixteen or more, or seventeen or more, or eighteen or more, or nineteen or more, or twenty or more, or twenty-one or more, or twenty-two or more, or twenty-three or more, or twenty-four or more, or all of miR-573, miR-512-3p, miR-20a-5p, miR-200b-3p, miR-20b-5p, miR-2115-3p, miR-466, miR-3137, miR-510-5p, miR-4267, miR-515-3p, miR-24-2-5p, miR-3117-3p, miR-668-3p, miR-132-3p, let-7e-5p, miR-3074-3p, miR-4260, miR-4288, miR-936, miR-4254, miR-148b-3p, miR-378b, miR-2909, or miR-193a-5p in the sample of exosomes.

6. The method of claim 1, further comprising administering to the subject one or more of: an antibiotic drug, an anti-inflammation drug, an immunosuppressive drug, a diuretic drug, a vitamin A, a vitamin D, a vitamin E, a vitamin K, a drug for a metabolic disease, or a drug to prevent ammonia accumulation.

7. The method of claim 1, wherein the antiviral drug for HBV comprises one or more of: interferon alpha, pegylated interferon, lamivudine, adefovir dipivoxil, telbivudine, or tenofovir.

8. The method of claim 1, wherein the sample of exosomes is isolated using size exclusion chromatography, filtration or immunosorbent capture.

9. The method of claim 1, wherein the sample of exosomes comprises whole exosomes or an exosome lysate.

10. The method of claim 3, wherein the determining step comprises labeling the one or more of miR-582-3p, miR-22-3p, let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-3679-5p, miR-616-3p, miR-668-3p, miR-7-2-3p, miR-196a-3p, miR-538b-5p, miR-34b-3p, miR-892a, or miR-500a-5p with a detectable label, wherein the detectable label is not a detectable polynucleotide.

11. The method of claim 3, wherein the determining step comprises capturing the one or more of miR-582-3p, miR-22-3p, let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-3679-5p, miR-616-3p, miR-668-3p, miR-7-2-3p, miR-196a-3p, miR-538b-5p, miR-34b-3p, miR-892a, or miR-500a-5p with one or more polynucleotide probe that selectively binds each of the one or more of miR-582-3p, miR-22-3p, let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-3679-5p, miR-616-3p, miR-668-3p, miR-7-2-3p, miR-196a-3p, miR-538b-5p, miR-34b-3p, miR-892a, or miR-500a-5p.

12. The method of claim 3, wherein the determining step comprises using a real-time polymerase chain reaction or a nucleic acid array.

13. The method of claim 1, wherein the antiviral drug for HBV comprises entecavir.

14. The method of claim 13, wherein the antiviral drug for HBV further comprises pegylated interferon.

15. A method of treating a subject suffering from an hepatitis B (HBV) induced liver fibrosis, comprising administering a therapy comprising entecavir to the subject selected by having a differential expression of at least two fold or more of microRNA(miR) 582-3p, and miR-22-3p in a sample of exosomes isolated from a body fluid of the subject compared to a control.

16. The method of claim 15, wherein the therapy further comprises one or more of an antibiotic drug, an anti-inflammation drug, an antiviral drug that does not comprise entecavir, an immunosuppressive drug, a diuretic drug, a vitamin A, a vitamin D, a vitamin E, a vitamin K, a drug for a metabolic disease, or a drug to prevent ammonia accumulation.

17. The method of claim 16, wherein the antiviral drug comprises one or more of: interferon alpha, pegylated interferon, lamivudine, adefovir dipivoxil, telbivudine, or tenofovir.

18. The method of claim 15, wherein the sample of exosomes further comprises a differential expression of one or more of: miR-let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-3679-5p, miR-616-3p, miR-668-3p, miR-7-2-3p, miR-196a-3p, miR-538b-5p, miR-34b-3p, miR-892a, or miR-500a-5p, of at least 2 fold, at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control.

19. The method of claim 15, wherein the sample of exosomes lacks a differential expression of one or more: miR-573, miR-512-3p, miR-20a-5p, miR-200b-3p, miR-20b-5p, miR-2115-3p, miR-466, miR-3137, miR-510-5p, miR-4267, miR-515-3p, miR-24-2-5p, miR-3117-3p, miR-668-3p, miR-132-3p, let-7e-5p, miR-3074-3p, miR-4260, miR-4288, miR-936, miR-4254, miR-148b-3p, miR-378b, miR-2909, or miR-193a-5p, of at least 2 fold, at least 2.5 fold, at least 3 fold, at least 3.5 fold, at least 4.5 fold, at least 5 fold, at least 6 fold, at least 7 fold, at least 8 fold, at least 9 fold, at least 10 fold, at least 11 fold, at least 12 fold, at least 13 fold, at least 14 fold, or at least 15 fold, compared to a control.

20. The method of claim 15, further comprising determining the expression level of one or more of miR-582-3p, miR-22-3p, let-7a-5p, miR-889-3p, miR-3200-3p, miR-642b-3p, let-7c-5p, let-7f-5p, miR-148s-3p, miR-16-5p, let-7g-5p, miR-26a-5p, miR-122-5p, miR-195-5p, miR-29c-3p, miR-139-5p, miR-509-5p, miR-27b-3p, miR-194-5p, let-7b-5p, miR-191-3p, miR-378a-3p, miR-3939, miR-2114-3p, miR-188-3p, miR-106b-30, miR-942-5p, miR-632, miR-370-3p, miR-566, miR-15b-5p, miR-548d-3p, miR-147a, miR-7-1-3p, miR-936, miR-551b-5p, miR-36'79-5p, miR-616-3p, miR-668-3p, miR-7-2-3p, miR-196a-3p, miR-538b-5p, miR-34b-3p, miR-892a, miR-500a-5p, miR-573, miR-512-3p, miR-20a-5p, miR-200b-3p, miR-20b-5p, miR-2115-3p, miR-466, miR-3137, miR-510-5p, miR-4267, miR-515-3p, miR-24-2-5p, miR-3117-3p, miR-668-3p, miR-132-3p, let-7e-5p, miR-3074-3p, miR-4260, miR-4288, miR-936, miR-4254, miR-148b-3p, miR-378b, miR-2909, or miR-193a-5p in the sample of exosomes.

21. The method of claim 1, wherein the body fluid comprises one or more of: urine, blood, saliva, breast milk, lymphatic fluid, serum or plasma.

* * * * *